United States Patent [19]

Marshall

[11] Patent Number: 4,748,113
[45] Date of Patent: May 31, 1988

[54] COMPOSITIONS AND METHODS FOR THE DIAGNOSIS OF GASTROINTESTINAL DISORDERS INVOLVING UREASE

[76] Inventor: Barry J. Marshall, 25 Bondi Street, Mount Hawthorn, 6016 Perth, Australia

[21] Appl. No.: 744,840

[22] Filed: Jun. 13, 1985

[51] Int. Cl.$^4$ ............................................. C12Q 1/58
[52] U.S. Cl. ..................................................... 435/12
[58] Field of Search ......................................... 435/12

[56] References Cited

U.S. PATENT DOCUMENTS

| | | | |
|---|---|---|---|
| 3,145,086 | 8/1964 | Free et al. | |
| 3,247,051 | 4/1966 | Leebrick | 167/22 |
| 3,873,269 | 3/1975 | Kraffczyk et al. | 435/12 |
| 4,016,268 | 4/1977 | Goldenberg et al. | 424/231 |
| 4,101,382 | 7/1978 | Chang | 435/12 |
| 4,153,685 | 5/1979 | Serfontein | 424/94 |
| 4,282,316 | 8/1981 | Modrovich | |

FOREIGN PATENT DOCUMENTS

| | | |
|---|---|---|
| 0018825 | 11/1980 | European Pat. Off. |
| 5877M | 4/1968 | France |
| 2442268 | 11/1979 | France |
| 58-77663 | 5/1983 | Japan |
| 1112251 | 5/1968 | United Kingdom |
| 1478742 | 7/1977 | United Kingdom |

OTHER PUBLICATIONS

Ruzicka et al.—Analytical Chemistry, vol. 51, (1979), pp. 199–203.

Hazel et al.—Lancet—Jul. 5, 1986, pp. 15–17.

A. Freedberg et al., "The Presence of Spirochetes in Human Gastric Mucosa", 7 *American Journal of Digestive Diseases*, pp. 443–445 (1940).

M. Goldenberg et al., "Protective Effects of Pepto-Bismol Liquid on the Gastric Mucosa of Rats", 69 *Gastroenterology*, pp. 636–640 (1975).

M. Steinhoff et al., "Bismuth Subsalicylate Therapy of Viral Gastroenteritis", 78 *Gastroenterology*, pp. 1495–1499 (1980).

M. Blaser et al., "Campylobacter Enteritis", 305 *New England Journal of Medicine*, pp. 1444–1452 (1981).

J. Koo et al., "Selective Coating of Gastric Ulcer by Tripotassium Dicitrato Bismuthate in the Rat", 82 *Gastroenterology*, pp. 864–870 (1982).

M. Gregory, "The Effect of Tri-Potassium Di-citrato Bismuthate on the Duodenal Mucosa During Ulceration", 62 *S.A. Medical Journal*, pp. 52–55 (1982).

J. Warren, "Unidentified Curved Bacilli on Gastric Epithelium in Active Chronic Gastitis", 1 *Lancet*, pp. 1273–1275 (1983).

B. Marshall, "Unidentified Curved Bacilli on Gastric Epithelium in Active Chronic Gastitis",1 *Lancet*, pp. 1273–1275 (1983).

Z. Zheng et al., "A Double-blind Short-term Clinical Trial of the Effect of Furazolidone on Peptic Ulcer", 23 *Chinese J. of Int. Medicine*, pp. 195–197 (1984).

(List continued on next page.)

*Primary Examiner*—Sam Rosen
*Attorney, Agent, or Firm*—Dennison, Meserole, Pollack & Scheiner

[57] ABSTRACT

Compositions for diagnosis of gastrointestinal disorders comprising urea, a bactericide, an indicator having a $pK_a$ of from about 6.5 to about 8.5, and water, wherein the composition has a pH of from about 5.0 to about 6.5 and wherein the pH is at least about one pH unit lower than the $pK_a$ of the indicator. Preferably the compositions contain a gelling agent, such as agar. Also preferably the composition contain a buffer. The invention also provides methods for diagnosis of gastrointestinal disorders in a human or lower animal subject, comprising the steps of obtaining a sample of gastric material from the subject, contacting the sample with a composition of this invention, and observing any color change, wherein a color change indicates the presence of a gastrointestinal disorder. Also provided are devices for use in diagnosis of gastrointestinal disorders.

10 Claims, 1 Drawing Sheet

OTHER PUBLICATIONS

C. McNulty et al., "Spiral Bacteria of the Gastric Antrum", 1 *Lancet*, pp. 1068 (1984).

B. Marshall et al., "Unidentified Curved Bacilli in the Stomach of Patients with Gastritis and Peptic Ulceration", 1 *Lancet*, pp. 1311-1315 (1984).

M. Langenberg et al., "Campylobacter-like Organisms in the Stomach of Patients and Healthy Individuals", 1 *Lancet*, p. 1348 (1984).

R. Burnett et al., "Campylobacter-like Organisms in the Stomach of Patients and Healthy Individuals", 1 *Lancet*, p. 1349 (1984).

B. Marshall et al., "Pyloric Campylobacter Serology", 2 *Lancet* p. 281 (1984).

A. McLean et al., "Microbes, Peptic Ulcer and Relapse Rates with Different Drugs", 2 *Lancet*, pp. 525-526 (1984).

B. Marshall et al., "Pyloric Campylobacter Infection and Gastroduodenal Disease", 142 *Medical Journal of Australia*, pp. 439-444 (1985).

Z. Zheng et al., "Double-blind Short-term Trial of Furazolidone in Peptic Ulcer", 1 *Lancet*, pp. 1048-1049 (1985).

C. McNulty et al., "Rapid Diagnosis of Campylobacter-Associated Gastritis", 1 *Lancet* pp. 1443-1444 (1985).

COMPOSITIONS AND METHODS FOR THE DIAGNOSIS OF GASTROINTESTINAL DISORDERS INVOLVING UREASE

BACKGROUND OF THE INVENTION

This invention relates to compositions and methods for the diagnosis of gastrointestinal disorders in humans and other animals.

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental, and psychogenic factors. Accordingly, the diagnosis and management of these disorders can be exceptionally difficult. A detailed discussion of gastrointestinal tract functions, disorders, causes, and treatments can be found in Spiro, *Clinical Gastroenterology* (3d. edition 1983).

Among the chronic disorders of the upper gastrointestinal tract are those which fall under the general categories of gastritis and peptic ulcer disease. (The upper gastrointestinal tract is generally defined as including the esophagus, the stomach, the duodenum, the jejunum, and ilium.) Peptic ulcers are lesions of the gastrointestinal tract lining, characterized by loss of tissue due to the action of digestive acids and pepsin. It has been generally held that peptic ulcers are caused either by gastric hypersecretion, or (more often) by decreased resistance of the gastric lining to digestive acids and pepsin. Gastritis is, by definition, typified by an inflammation of the stomach mucosa. In practice, though, the disorder is manifested by a broad range of poorly-defined, and heretofore inadequately treated, symptoms such as indigestion, "heart burn", dyspepsia and excessive eructation. A general discussion of gastritis appears in B. J. Marshall and J. R. Warren, "Unidentified Curved Bacilli in the Stomach of Patients with Gastritis and Peptic Ulceration", *The Lancet*, 1311-1315 (1984), and in R. Greenlaw, et al., "Gastroduodenitis, A Broader Concept of Peptic Ulcer Disease", 25 *Digestive Diseases and Sciences* 660-672 (1980).

As with the management of any disorder, the rapid, precise, and accurate diagnosis of gastrointestinal disorders is of paramount importance. However, the diagnostic methods typically employed in the art are often slow, cumbersome, costly and may yield equivocal or inaccurate results. See, e.g., Spiro, supra.

It has been discovered that many disorders affecting the upper gastrointestinal tract are mediated by bacteria, such as those of the genus Campylobacter. Further, it has now been discovered that gastrointestinal disorders of the upper gastrointestinal tract may be detected and diagnosed by methods and compositions for the detection urease enzyme in the gastric mucosa or gastric fluid of humans or lower animals. The methods and compositions of this invention thus provide a rapid, inexpensive, and accurate diagnosis of such gastrointestinal disorders.

SUMMARY OF THE INVENTION

The present invention provides compositions and methods for the diagnosis of gastrointestinal disorders in humans or lower animals. The compositions of this invention comprise:

(a) urea, at a concentration of from about 10 to about 40 grams per liter;
(b) a bactericide, at a concentration of from about 1 to about 5 grams per liter;
(c) an indicator having a $pK_a$ of from about 6.5 to about 8.5, at an effective concentration; and
(d) water;

wherein said composition has a pH of from about 5.0 to about 6.5, and the pH of said composition is at least about one pH unit lower than the $pK_a$ of said indicator. Preferably, these compositions are in gel form, containing a gelling agent at a concentration of from about 5 to about 50 grams per liter. The methods of this invention, for the detection of gastrointestinal disorders in a human or lower animal subject, comprise the steps of obtaining a sample of gastric material from said subject, contacting said sample with a composition of the present invention, and observing any color change in said composition.

DESCRIPTION OF THE DRAWINGS

The attached drawings are of a preferred test device useful in the methods of the present invention. In particular.

Figure 1:
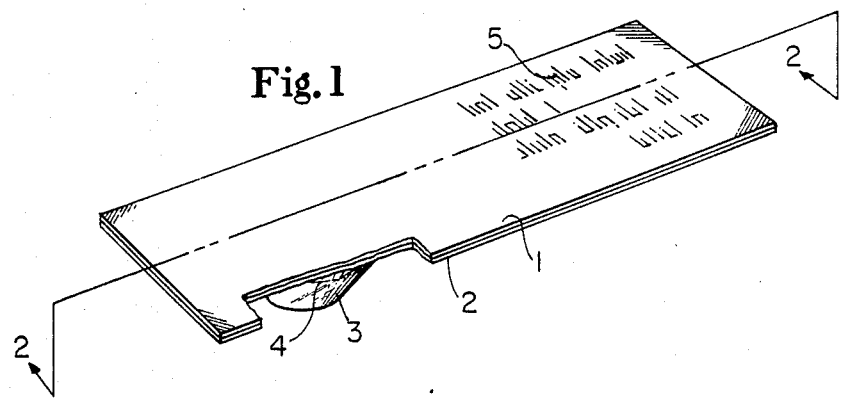
FIG. 1 is an isometric view of a test device of this invention, with a cutaway exposing a container containing a composition of this invention.

A more detailed description of the drawings is set forth in the "Devices" subsection of the Description of the Invention, below.

DESCRIPTION OF THE INVENTION

Composition and Essential Components

The present invention provides composition and methods for the diagnosis of gastrointestinal disorders in humans and lower animals.

The compositions of this invention comprise:

(a) urea, at a concentration of from about 10 to about 40 grams per liter;
(b) bactericide, at a concentration of from about 1 to about 5 grams per liter;
(c) an indicator having a $pK_a$ of from about 6.5 to about 8.5, at an effective concentration; and
(d) water;

wherein said composition has a pH of from about 5.0 to about 6.5, and the pH of said composition is at least about one pH unit lower than the $pK_a$ of said indicator. (All concentrations herein are by weight of component per volume of total composition.)

As used herein, "an effective concentration" of indicator is a concentration of indicator which effects a readily-discernable color of the composition of this invention when used according to the processes of this invention. Typically, the indicator is present at a level of from about 2 to about 100 milligrams per liter. Preferably, the compositions contain urea of a concentration of from about 20 to about 40 grams per liter.

As used herein, "gastrointestinal disorder" encompasses any disease or other disorder of the gastrointestinal tract of a human or lower animal. Such gastrointestinal disorders include, for example: disorders not manifested by presence of ulcerations in the gastric mucosa (herein "non-ulcerative gastrointestinal disorder"), including chronic or atrophic gastritis, gastroenteritis, non-ulcer dyspepsia, esophogeal reflux disease and gastric motility disorders; and "peptic ulcer disease", i.e., gastric and duodenal ulcers. In particular, "gastrointestinal disorder" refers to such disorders of the upper gastrointestinal tract caused or mediated by bacteria, including campylobacter-like organisms (herein "CLO"), e.g., *Campylobacter pyloridis*. Such CLO include those described in J. R. Warren and B. J. Marshall, "Unidentified Curved Bacilli on Gastric Epithelium in Active Chronic Gastritis", *The Lancet* 1273-1275 (1983), incorporated by reference herein, and G. Kasper and N. Dickgiesser, "Isolation from Gastric Epithelium of Campylobacter-like Bacteria that are Distinct from 'Campylobacter Pyloridis'", *The Lancet* 111-112 (1985).

Urea is of the formula $H_2NCONH_2$, and is a naturally occurring product of protein metabolism. Urea for use in the compositions of this invention is available from a variety commercial sources. As a basis for this invention, it has been found that gastric materials from humans or other animals having gastrointestinal disorders contain relatively large quantities of urease (urea amidohydrolase), which hydrolizes urea to ammonium carbonate, or ammonia and carbon dioxide. The compositions of this invention serve, in part, to detect the presence of urease through its hydrolysis of urea.

The indicators useful in this invention are weak acids, with sharply different colors in their dissociated (ionized) and undissociated (neutral) states. The indicators useful herein have $pK_a$ values of from about 6.5 to about 8.5, preferably from about 7.0 to about 8.0. The color exhibited by the indicator in the present composition will depend upon the pH of the composition, the particular indicator used, and the dissociation constant ($K_a$) for that indicator (i.e., $pK_a = \log_{10} K_a$). As the color exhibited by the indicator changes over a range of pH values ($pH = \log_{10}[H^+]$), the indicators useful in the present compositions change color over a pH range of from about 5.5 to about 9.0, preferably from about 6.5 to about 8.5. The pH of the present compositions are, accordingly, adjusted to a pH at least about one pH unit lower than the $pK_a$ of the indicator used (i.e., having a hydrogen ion concentration [H+] ten times less than (10% of) the hydrogren ion concentration in a solution having a pH equal to the $pK_a$ of the indicator). Preferably, the pH is adjusted to a pH about two pH units below the $pK_a$ of the indicator. Adjustment of the pH of the present compositions can be effected by addition of a base (e.g., sodium hydroxide) or an acid (e.g., hydrochloric acid or citric acid). Thus, preferably, the pH of the composition of this invention is adjusted to a pH of from about 5.0 to about 6.5, more preferably from about 5.0 to about 6.0.

Indicators among those useful herein include p-nitrophenol, bromothymol blue (dibromothymolsulfonphthalein), phenol red (phenolsulfonphthalein) neutral red (2-methyl-3-amino-6-dimethylaminophenazine), quinoline blue (cyanine), cresol red (o-cresolsulfonphthalein), matacresol purple (m-cresolsulfonphthalein), and thymol blue (thymolsulfonphthalein). Bromothymol blue, phenol red, neutral red and cresol red are preferred indicators for use in the compositions of this invention. Indicators among those useful herein are described in the *The Merck Index* (9th ed. 1976), incorporated by reference herein.

The bactericide incorporated in the compositions of this invention is one or more materials which substantially inhibit the growth of urease-producing organisms in the composition. Bactericides useful in this invention include sodium azide and methylhydroxybenzoate. Methylhydroxybenzoate is a particularly preferred bactericide. The specific amount of bactericide to be used in this present compositions depends upon factors well known in the microbiological arts, such as the particular bactericide used, and the bactericidial properties (if any) of the other components in the present compositions.

Optional Components

The compositions of this invention may contain optional components which affect the performance or physical characteristics of the compositions. Such additional components must not, however, interfere with the indicator, as by obscuring the colors exhibited by the indicator.

The compositions of this invention preferably contain a gelling agent, so that the compositions are in a semisolid state at ambient conditions. A particularly preferred gelling agent is agar, present at a level of from about 5 to about 50 grams per liter, preferably from about 10 to about 20 grams per liter. The agar used in the compositions of this invention is readily available from a variety of commercial sources. Typically, agar (a polysaccharide complex) is extracted from the agarocytes of certain algae. Also, preferably, the agar used in the present composition is nonnutritive, i.e., does not support the growth of microorganisms.

A particularly preferred optional component of the present invention is a buffer. As stated above, the compositions of this invention are adjusted to a pH at least one pH unit below the $pK_a$ of the indicator used. Thus, preferably, the pH of the present composition is from about 5.0 to about 6.5, more preferably from about 5.0 to about 6.0. This pH of the final composition is preferably effected by the addition of a suitable buffer. Such buffers are well known in the chemical art, including the use of such weak acid salts as sodium bisulfate, sodium acetate and sodium phosphate.

The total amount of buffer incorporated in the present composition will depend upon the total amount of urea incorporated in the composition, such that the buffer does not prevent sufficient change in composition pH (resulting from hydrolysis of the urea present) so as to cause a change in the color of the indicator used. However, the buffer is preferably present in a concentration sufficient to prevent substantial changes in composition pH, and (thereby) spurious indicator color changes, due to chemicals other than urease enzyme in the gastric material sample to be analyzed. Typically, then, the buffer is incorporated in the present composition of concentrations of from about 50 to about 2000 milligrams per liter. (As used herein, the buffer concentration includes the concentration of the buffer salt and of the acid used to effect pH adjustment of the composition.)

Methods

This invention provides methods for the detection of a gastrointestinal disorder in a human or lower animal subject, comprising the steps of:

(a) obtaining a sample of gastric material from said subject;

(b) contacting said sample with a composition of this invention; and (c) observing the color of said composition;

wherein a change of color of said composition indicates the existence of a gastrointestinal disorder in said subject.

As used herein, "gastric material" refers to any material obtained directly or indirectly from the upper gastrointestinal tract of a human or other animal. Such materials include, for example, gastric epithelium, gastric mucosa, and digestive fluids. Samples of such materials, for use in the methods of this invention, may be obtained by any of a variety of well known methods, according to sound medical practice. Such methods include, for example, obtaining the sample by biopsy of the subject, obtaining the sample from the vomitus of the subject, and obtaining the sample from nasal gastric aspirate.

As used herein, "contacting" the sample with the composition of the present invention, as in step 2 of the process set forth above, refers to any method which effects substantial interface between a composition of this invention and the sample gastric material, for a time sufficiently long so as to allow the hydrolysis of urea by any urease present in the sample. Such time is typically longer than about five minutes. Preferably, though, the gastric material sample is immersed, or substantially immersed, in a composition of this invention. Also, preferably, care is taken so as to avoid contamination of the gastric material sample with organisms from a source other than the stomach of the subject to be diagnosed.

In the event that the gastric material used constitutes digestive fluids, then a preferred optional step in the present processes is testing the pH of said gastric material. Preferably, then, the sample is contacted with a pH-test composition which is an aqueous solution of the particular indicator used in said composition of this invention (without urea), adjusted to the same pH as said urea-containing composition of this invention. If the gastric material effects no change in the indicator color of the pH-test composition, then the material is of an acid pH, and may be used directly in the contacting step of the process of this invention described above. If, however, the color of the pH-test composition changes, then the pH of the gastric material must be acidified, as by addition of an acid.

The observing step of this process entails detection of any color change in the composition color, to the color exhibited by the indicator in its dissociated state. Failure of the composition to change color after about twenty-four hours reflects a negative test result.

Devices

The methods of this invention are preferably performed using a device, herein "diagnostic device", which contains a quantity of a composition of this invention in an easily-handled container. Such devices of this invention comprise:

(a) a container, having an opening aperture area of from about 20 square millimeters to about 200 square millimeters and having a total contained volume of from about 40 cubic millimeters to about 1000 cubic millimeters; and (b) a cover for said container, affixed to said container by a means which allows said cover to be moved so as to open and close said container opening;
wherein said container contains from about 0.04 to about 2.0 milliliters of a composition of this invention. Preferably, the container contains from about 0.40 milliliters to about 0.60 milliliters of a composition of this invention.

Figure 2:
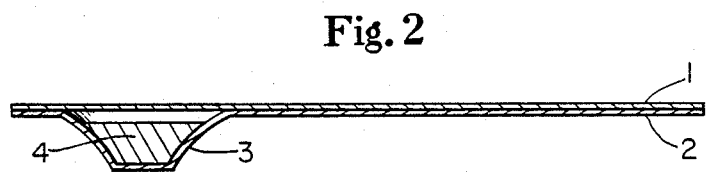
FIG. 2 is a sectional view of the device of FIG. 1.
Figure 3:
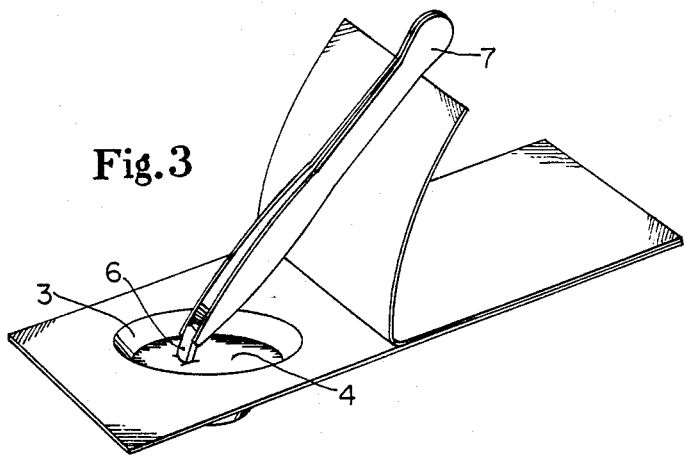
FIG. 3 is an isometric view of the device of FIG. 1, showing the device in use.

One such preferred diagnostic device is pictured in FIGS. 1 through 3 of the Drawings. FIG. 1 and FIG. 2 show a container 3 which is formed as a concave form, or well, in a continuous, flat holder 2, which is a sheet of rigid, or semi-rigid, water-impermeable material. The container contains a composition of this invention 4. A cover 1, is affixed to the container, and made of a flexible, water-impermeable material, and is of the same dimensions as the rigid holder sheet 2. As shown in FIG. 1, a label 5 is preferably affixed to or printed directly on the flexible cover 1. FIG. 3 shows the diagnostic device with the flexible cover partially removed, opening the container 3, thereby allowing a sample of gastric material 6 to be placed in the test composition 4 using a suitable device, such as a forceps 7.

The flexible cover 1 is affixed to the rigid container/holder material 2 by a means allowing its removal, and opening and closing of the container, such as by an adhesive which remains functional (tacky) throughout repeated openings and closings of the container. Preferably the cover material is sufficiently thin so as to allow piercing by a syringe and injection of a liquid gastric material directly into the composition, without opening the cover.

The following non-limiting examples illustrate the compositions, methods and devices of the present invention.

EXAMPLE I

A composition, according to this invention, was made comprising the following components:

| Component | Quantity (grams) | Final Concentration |
| --- | --- | --- |
| urea | 3.000 | .30 g/l |
| phenol red* | 0.008 | 80 mg/l |
| methyl hydroxy benzoate | 0.200 | .2 g/l |
| bacteriological agar | 1.500 | 15 g/l |
| citric acid | 0.040 | 400 mg/l |
| sodium phosphate | 0.080 | 800 mg/l |

*phenol sulfonphthalein indicator, having $pK_a = 7.9$, exhibiting a yellow color in undissociated state (below pH 6.4) and red color in dissociated state (above pH 8.2)

The components, except urea, were dissolved in 100 milliliters of water, heated to approximately 65° C., and stirred until the solution was clear. The solution was then cooled to below approximately 45° C., the urea added and stirred, and the solution pH was measured to be 6.0. The composition was then poured into containers, in a device of this invention, each container receiving approximately 0.5 milliliters of the composition. The composition was allowed to cool to ambient temperature, forming a gel in the container and having a deep yellow color.

A composition made as above is used in a process of this invention, by obtaining a sample of gastric mucosa from the stomach of a human subject presenting symptons of gastritis. The mucosa sample is then inserted into the composition and the color observed. After approximately 15 minutes, a red color is observed, indicating the presence of CLO-mediated gastrointestinal disorder.

EXAMPLE II

A composition is made, according to the present invention, comprising the following components:

| Component | Quantity (grams) | Final Concentration |
|---|---|---|
| urea | 2.000 | 20 g/l |
| phenol red | 0.006 | 60 mg/l |
| soduim azide | 0.100 | 1 g/l |
| agar | 2.000 | 20 g/l |

The components are dissolved in 100 ml water, heated to 65° C., and the pH adjusted to pH 5.50. Approximately 0.5 milliliters of the composition is poured into the container of a device of this invention and allowed to cool, forming a gel.

The composition and device are used in a process of this invention by obtaining a sample of vomitus from a human infant subject suspected of having gastritis. A sample of the vomitus is drawn into a syringe, and a portion injected into a pH-test composition comprising 0.6 milligrams of phenol red in 10 ml of water, adjusted to pH 5.5. The color of the pH-test composition does not change. Thereafter, the remainder of the vomitus sample is injected into the composition of this invention, by piercing the cover of the device. The color is observed for approximately 20 minutes, noting a change in color from deep yellow to red, and indicating the presence of gastrointestinal disorder.

What is claimed is:

1. A composition for the diagnosis of gastrointestinal disorders in a human or lower animal subject by detection of urease in gastric material of the subject, comprising:
   (a) urea, at a concentration of from about 10 to about 40 grams per liter;
   (b) a bactericide which substantially inhibits the growth of urease-producing organisms, at a concentration of from about 1 to about 5 grams per liter;
   (c) an indicator having a $pK_a$ of from about 6.5 to about 8.5, at an effective concentration; and
   (d) water;
   wherein said composition has a pH of from about 5.0 to about 6.5, and the pH of said composition is at least about one pH unit lower than the $pK_a$ of said indicator.

2. A composition, according to claim 1, wherein said indicator is present at a concentration of from about 2 to about 100 milligrams per liter.

3. A composition, according to claim 2, wherein said indicator has a $pK_a$ of from about 7.0 to about 8.0.

4. A composition, according to claim 3, wherein said indicator is phenol red.

5. A composition, according to claim 3, wherein said composition has a pH of from about 5.0 to about 6.0.

6. A composition, according to claim 1, additionally comprising a buffer.

7. A composition, according to claim 1, additionally comprising a gelling agent, at a concentration of from about 5 to about 50 grams per liter.

8. A composition, according to claim 7, wherein said gelling agent is a non-nutritive agar.

9. A composition, according to claim 8, wherein said agar is present at a concentration of from about 10 to about 20 grams per liter.

10. A method for detection of a gastrointestinal disorder in a human or lower animal subject by detection of urease in gastric material of the subject, comprising the steps of:
   (a) obtaining a sample of gastric material from said subject;
   (b) contacting said sample with a composition comprising:
   urea, at a concentration of about 10 to about 40 grams per liter;
   a bactericide which substantially inhibits the growth of urease-producing organisms, at a concentration of about 1 to about 5 grams per liter;
   an indicator having a $pK_a$ of about 6.5 to about 8.5, at an effective concentration; and
   water;
   said composition having a pH of about 5.0 to about 6.5, said pH being about one pH unit less than the $pK_a$ of said indicator; and
   (c) observing the color of said composition; wherein a change of color of said composition indicates the presence of urease and the existence of a gastrointestinal disorder in the subject.

* * * * *